(12) United States Patent
Holley et al.

(10) Patent No.: US 8,696,128 B2
(45) Date of Patent: Apr. 15, 2014

(54) OPTICAL MEASUREMENT APPARATUS AND METHOD THEREFOR

(75) Inventors: Richard Holley, Maidenhead (GB); Robin Taylor, Twyford (GB)

(73) Assignee: Lein Applied Diagnostics, Berkshire (GB)

( * ) Notice: Subject to any disclaimer, the term of this patent is extended or adjusted under 35 U.S.C. 154(b) by 105 days.

(21) Appl. No.: 12/671,155

(22) PCT Filed: Jul. 29, 2008

(86) PCT No.: PCT/GB2008/050636
§ 371 (c)(1),
(2), (4) Date: May 10, 2010

(87) PCT Pub. No.: WO2009/016405
PCT Pub. Date: Feb. 5, 2009

(65) Prior Publication Data
US 2010/0253911 A1    Oct. 7, 2010

(30) Foreign Application Priority Data

Jul. 30, 2007    (GB) .................................. 0714739.0

(51) Int. Cl.
*A61B 3/10*    (2006.01)
*A61B 3/02*    (2006.01)
*G01B 11/26*    (2006.01)
*G01C 1/00*    (2006.01)

(52) U.S. Cl.
USPC .......................... 351/221; 351/243; 356/141.4

(58) Field of Classification Search
USPC .................... 351/200, 205, 221, 222
See application file for complete search history.

(56) References Cited

U.S. PATENT DOCUMENTS

| | | | |
|---|---|---|---|
| 3,567,325 A | 3/1971 | Smith-Vaniz |
| 3,963,019 A | 6/1976 | Quandt |
| 4,014,321 A | 3/1977 | March |
| 4,154,114 A | 5/1979 | Katz et al. |
| 4,407,008 A | 9/1983 | Schmidt et al. |
| 4,750,830 A | 6/1988 | Lee |
| 4,806,004 A | 2/1989 | Wayland |
| 5,209,231 A | 5/1993 | Cote et al. |

(Continued)

FOREIGN PATENT DOCUMENTS

| | | |
|---|---|---|
| DE | 4321796 A1 | 1/1994 |
| DE | 19632594 A1 | 2/1998 |

(Continued)

OTHER PUBLICATIONS

PCT Search Report for PCT/GB2008/050636; Feb. 13, 2009.

*Primary Examiner* — Thomas K Pham
*Assistant Examiner* — Brandi Thomas
(74) *Attorney, Agent, or Firm* — Bracewell & Giuliani LLP (57) ABSTRACT

An optical measurement apparatus comprises an optical system (100) having a receiving axis (115). The optical system (100) comprises a source (102) that generates a probe beam that is directed to a location to be measured (114). A detector (112) of the optical system receives a reflected beam from the location to be measured (114). The apparatus also comprises a processing resource that receives an output signal from the detector (112) and makes an assessment of a characteristic of the output signal in order to determine a degree of alignment of the location to be measured (114) with the receiving axis (115) of the optical system (100).

18 Claims, 5 Drawing Sheets

(56) References Cited

U.S. PATENT DOCUMENTS

| | | |
|---|---|---|
| 5,433,197 A | 7/1995 | Stark |
| 5,582,168 A | 12/1996 | Samuels et al. |
| 5,668,621 A | 9/1997 | Nanjo |
| 5,785,651 A | 7/1998 | Kuhn et al. |
| 6,066,847 A | 5/2000 | Rosenthal |
| 6,152,875 A | 11/2000 | Hakamata |
| 6,181,957 B1 | 1/2001 | Lambert et al. |
| 6,187,599 B1 | 2/2001 | Asher et al. |
| 6,188,477 B1 | 2/2001 | Pu et al. |
| 6,226,089 B1 | 5/2001 | Hakamata |
| 6,267,477 B1 | 7/2001 | Karpol et al. |
| 6,382,794 B1 | 5/2002 | Lai et al. |
| 6,424,850 B1 | 7/2002 | Lambert et al. |
| 6,442,410 B1 | 8/2002 | Steffes |
| 6,574,501 B2 | 6/2003 | Lambert et al. |
| 6,715,877 B2 * | 4/2004 | Molebny ............ 351/211 |
| 6,749,302 B2 * | 6/2004 | Percival et al. ......... 351/208 |
| 6,836,337 B2 | 12/2004 | Cornsweet |
| 6,853,854 B1 | 2/2005 | Proniewicz et al. |
| 6,934,035 B2 | 8/2005 | Yang et al. |
| 7,145,645 B2 * | 12/2006 | Blumenfeld et al. .......... 356/73 |
| 2002/0171804 A1 | 11/2002 | Rathjen |
| 2003/0225321 A1 | 12/2003 | Cote et al. |
| 2003/0233036 A1 | 12/2003 | Ansari et al. |
| 2004/0080759 A1 | 4/2004 | Shaver |
| 2004/0087843 A1 | 5/2004 | Rice et al. |
| 2004/0138539 A1 | 7/2004 | Jay et al. |
| 2004/0152963 A1 | 8/2004 | March |
| 2004/0257585 A1 | 12/2004 | Cornsweet |
| 2006/0115199 A1 * | 6/2006 | Yao ............................ 385/11 |
| 2006/0200013 A1 | 9/2006 | Smith et al. |
| 2007/0285620 A1 * | 12/2007 | Clark ............................ 351/214 |

FOREIGN PATENT DOCUMENTS

| | | |
|---|---|---|
| EP | 0485803 A1 | 5/1992 |
| EP | 0589191 A1 | 3/1994 |
| EP | 0722692 A1 | 7/1996 |
| EP | 0792619 A1 | 9/1997 |
| EP | 0807812 A1 | 11/1997 |
| EP | 0810457 A1 | 12/1997 |
| GB | 1521113 | 8/1978 |
| GB | 2144537 A | 3/1985 |
| GB | 2407378 A | 4/2005 |
| GB | 2409033 A | 6/2005 |
| JP | 3055510 A | 3/1991 |
| JP | 05126769 A | 5/1993 |
| WO | WO92/01417 | 2/1992 |
| WO | WO93/07801 | 4/1993 |
| WO | WO97/13448 | 4/1997 |
| WO | WO97/30627 | 8/1997 |
| WO | WO99/44496 | 9/1999 |
| WO | WO00/60350 | 10/2000 |
| WO | WO0211612 A | 2/2002 |
| WO | WO02/087429 A1 | 11/2002 |
| WO | WO03/012486 A2 | 2/2003 |
| WO | WO03/087775 A2 | 10/2003 |
| WO | WO2004/030530 A1 | 4/2004 |
| WO | WO2004/034894 A1 | 4/2004 |
| WO | WO2004/064628 A1 | 8/2004 |
| WO | WO2005/120334 A1 | 12/2005 |

* cited by examiner

OPTICAL MEASUREMENT APPARATUS AND METHOD THEREFOR

RELATED APPLICATION

This application claims priority to PCT application PCT/GB2008/050636 filed Jul. 29, 2008, which claimed priority to British patent application GB 0714739.0 filed Jul. 30, 2007.

The present invention relates to an optical measurement apparatus of the type that, for example, is used to measure a physiological property of a body part, such as an eye. The present invention also relates to a method of optically measuring a location to be measured, the method being of the type that, for example, is used to measure a physiological property of a body part, such as an eye.

Diabetes is a major and rapidly growing problem with over 230 million people suffering from the disorder worldwide. In addition, studies have shown that the incidence of juvenile-onset, insulin-dependent diabetes has doubled over the last 15 years. There has also been a five fold increase in the number of children under the age of 5 suffering from diabetes in just 20 years.

The symptoms associated with diabetes can be severe. If the blood glucose level is not suitably controlled by the patient, the physical damage which may be caused includes blindness, heart disease and gangrene. As such, the mortality rate for people with diabetes is significantly higher than the rate for the average person.

A person's blood glucose concentration varies over a relatively short timescale, due to a number of factors, such as the length of time since the patient's last meal, the type of food ingested, the amount of exercise taken, and whether or not the patient is otherwise ill. As a result, people with diabetes usually need to test their glucose levels many times a day, in order to monitor and control their condition. The actual testing regime varies between patients and is individually prescribed by the doctor or diabetes educator of the patient.

The primary method used for testing blood glucose concentration involves the taking of a blood sample, which is then analysed. In this test, a patient's finger or arm is pricked with a small needle and the resulting drop of blood is placed on a test strip, for analysis in a hand-held meter. If the glucose concentration reading is above an acceptable level, insulin must be injected to bring the glucose concentration back within an acceptable range.

Due to the frequency of testing required to monitor the blood glucose concentration, the patient is normally expected to perform the tests throughout the day, drawing and analysing the blood sample himself. There are a number of problems experienced by patients with the above procedure. Firstly, the technique is invasive and therefore carries the risk of infection. Secondly, continual pricking of the fingers causes hard skin. Thirdly, the process is clearly not pain-free. Finally, there is a large, ongoing consumables cost associated with this method. As a result of these and other problems, certain sectors of the diabetic population do not test themselves as often as required. This is particularly the case for the elderly, who tend to lack the fine motor skills required; teenagers, who tend to find the whole procedure socially embarrassing; and children, who tend not to accept the discomfort associated with the process.

A number of non-invasive blood glucose concentration measuring techniques have been proposed to overcome these problems. In general these have been designed to work by making a measurement through the skin but the variability in the skin's characteristics have led to inaccurate results.

More recently the eye has been proposed as a better measurement location. Possible techniques for measuring glucose in the eye include spectroscopy on the conjunctiva (e.g. U.S. Pat. No. 6,975,892), psychophysical measurements on the fundus (e.g. U.S. Pat. No. 6,895,264), a contact lens or other implantable device that absorbs glucose (e.g. U.S. Pat. No. 6,980,842 or US 2006/0166350) or a measurement of the ocular refractive correction (e.g. U.S. Pat. No. 6,442,410).

One particular approach which has been suggested involves measuring the glucose concentration of the aqueous humour in the anterior chamber of the eye, since, while varying between individuals, there is a close correlation between this concentration and the blood glucose concentration. Measurement of the glucose concentration of the aqueous humour may be achieved by various means; for example, by polarimetry (e.g., U.S. Pat. No. 5,896,198); by Raman techniques (e.g., WO A 00/02479); by fluorescence photometry (e.g., WO 2005/120334); by spectrometry (e.g., U.S. Pat. No. 5,969,815); by fluorescence spectroscopy (e.g., WO 02/087429) or by reflectometry (e.g., U.S. Pat. No. 6,236,089).

A desirable alternative approach to measuring the glucose concentration in the aqueous humour involves measuring the refractive index of the aqueous humour, since there is a strong correlation between the refractive index and the glucose concentration. In this respect, U.S. Pat. No. 3,963,019, U.S. Pat. No. 6,152,875, WO 03/025562, WO 05/044099 and WO 05/058152 describe various techniques associated with measurement of the refractive index of the aqueous humour.

In addition there are many other measurements that require an instrument to be aligned to the eye of a patient or operator. In one example, it is necessary to measure the thickness or shape of the cornea in order to make Laser-Assisted in Situ Keratomileusis (LASIK) surgery safer (for example as described in U.S. Pat. No. 6,585,723 and US 2004/0080759). Alignment to the eye of a patient is also required during the measurement of ophthalmic characteristics such as Central Corneal Thickness (CCT), Anterior Chamber Depth (ACD), corneal curvature and/or axial length of the eye.

In all of the above cases, the measurement fidelity is compromised by variations in alignment between the meter and the patient's eye. In addition, for a successful personal use meter, it is important that the patient is able to use the meter by themselves, and align to the meter by themselves, without any clinician involvement. On the other hand, confirmation that the alignment is correct is desirable to clinicians.

Furthermore, at times it is not always possible to achieve good alignment to the eye when measuring glucose levels and other parameters of the eye non-invasively.

According to a first aspect of the present invention, there is provided an optical measurement apparatus comprising: an optical system comprising: a source arranged to generate, when in use, a probe beam, the optical system being arranged to direct, when in use, the probe beam to a location to be measured; a detector arranged to receive, when in use, a reflected beam from the location to be measured; and a receiving axis; wherein the apparatus further comprises: a processing resource operably coupled to the detector and capable of assessing when in use, a characteristic of an output generated by the detector, assessment of the characteristic of the output corresponding to an assessment of degree of alignment of the location to be measured with the receiving axis of the optical system.

The location to be measured may be a location of a feature of an eye.

The assessment of the characteristic may be a quantitative assessment of the characteristic of the output.

The assessment of the characteristic may be a qualitative assessment of the characteristic of the output.

The assessment of the characteristic of the output may be an assessment of a parameter measured and corresponding to the characteristic of the output.

The processing resource may be arranged to provide feedback information indicative of the degree of alignment of the location to be measured with the receiving axis, the feedback information being based upon the assessment of the characteristic of the output.

The eye may have a first axis and a second axis, the processing resource being arranged to provide feedback for obtaining a misalignment of the first axis with the receiving axis in order to achieve alignment of the second axis with the receiving axis.

The feedback information may be an audible or visual indication of alignment.

The probe beam may be invisible to the eye.

The processing resource may be arranged to perform a measurement in respect of the reflected beam and generate a first measure of the characteristic of the output.

The measure of the characteristic of the output may constitute the feedback information.

The first measure of the characteristic of the output may relate to one or more of: peak luminous intensity, tail luminous intensity, peak width, tail width, number of peaks, peak shape, peak location and/or inter-peak spacing. The measure may be any mathematical function, for example integrals or differentials, such as an integral of a profile or a differential of a profile.

The processing resource may be arranged to generate a second measure of another characteristic of the output.

The first measure may be used to provide a coarse indication of the degree of alignment of the location to be measured with the optical system.

The second measure may be used to provide a fine indication of the degree of alignment of the location to be measured with the optical system.

The apparatus may further comprise a store for storing data corresponding to a state of substantially optimum alignment with the optical system.

The output of the detector may have a signal profile corresponding to a reflection of the probe beam in respect of the location to be measured.

The apparatus may further comprise a store for storing reference profile data corresponding to at least part of a profile and/or reference characteristic data relating thereto, the reference profile data and/or the reference characteristic data corresponding to a state of alignment with the optical system.

The processing resource may be arranged to make the assessment based upon comparison of at least part of the signal profile and/or characteristic data relating thereto in respect of the output measured and the stored reference profile data and/or the stored reference characteristic data.

The output of the detector may be a trace comprising a number of profiles and/or characteristics respectively corresponding to a number of reflections of the probe beam.

The number of reflections may comprise a first reflection from the location to be measured and another location to be measured, the locations to be measured being misaligned with respect to each other.

The signal profile or the trace may be generated by acquiring a number of sequential profiles or traces over a period of time using the probe beam and processing a number of output signals corresponding to the sequential profiles or traces.

The processing of the number of output signals may comprises filtering the number of output signals so as to discard any output signals having respective degrees of alignment that do not conform to a predetermined alignment degree threshold rule.

The processing of the number of output signals may comprise averaging undiscarded output signals from the number of output signals.

A physiological body-part may comprise the location to be measured. The physiological body-part may be an eye.

According to a second aspect of the present invention, there is provided a method of optical measurement, comprising: generating a probe beam; directing the probe beam to a location to be measured; receiving via an optical system having a receiving axis a reflected beam from the location to be measured; and assessing a characteristic of an output signal corresponding to the reflected beam in order to determine degree of alignment of the location to be measured with the receiving axis of the optical system.

According to a third aspect of the present invention, there is provided a computer program element comprising computer program code means to make a computer execute the method as set forth above in relation to the second aspect of the invention.

The computer program element may be embodied on a computer readable medium.

It is thus possible to provide an apparatus and method that enables a measurement apparatus to be aligned with a location to be measured, for example a surface of the eye, and/or compensate for misalignment to determine the concentrations of other compounds in the eye, including both naturally occurring and intentionally introduced chemicals, and which may be used to measure other properties of the eye, such as the location of each surface or the thickness or location of the constituent elements of the eye or medical conditions visible in the eye.

At least one embodiment of the invention will now be described, by way of example only, with reference to the accompanying drawings, in which.

Throughout the following description identical reference numerals will be used to identify like parts.

Figure 1:
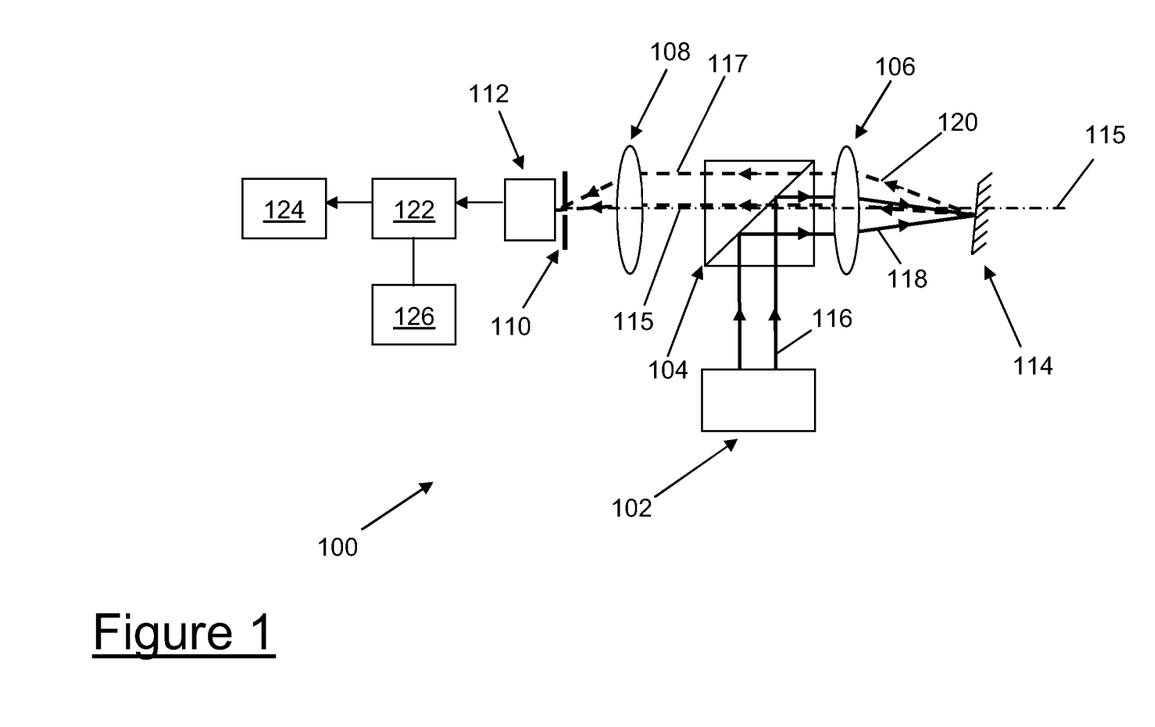
FIG. 1 is a schematic diagram of an apparatus constituting an embodiment of the invention.

Referring to FIG. 1, an optical measurement apparatus, for example a glucometer, comprises an optical system 100 including a source 102 of electromagnetic radiation, for example visible light, though light invisible to the eye, for example near infra-red light, can be used so as to reduce discomfort to the eye. An output window (not shown) of the source 102 is oriented towards a beamsplitter 104 that is placed in an optical path of the source 102. The beamsplitter 104 serves to fold the optical path of the source 102 towards a scanning lens 106. In this example, the scanning lens 106 is shown as a single lens, though the skilled person will appreciate a lens system can serve as the scanning lens 106 or any other suitable optical arrangement, scanning or non-scanning in nature for making measurements. The scanning lens 106 is capable of linearly translating so as to move closer to or further from the beamsplitter 104. The beamsplitter 104 is a half-silvered mirror, though the skilled person will appreciate that any suitable alternative optical element or arrangement can be employed to perform the function of the beamsplitter 104, for example a polarising beamsplitter and ¼ wave plate disposed between the polarising beam splitter and the scanning lens 106.

A focussing lens 108 is disposed opposite the beamsplitter 104 so that the beamsplitter 104 is located between the scanning lens 106 and the focussing lens 108. The optical measurement apparatus is a confocal system, and so an aperture 110 constituting a pinhole is disposed opposite the focussing lens 108, a detector 112 being disposed adjacent the aperture 110. The detector 112, in this example, comprises a photodiode (not shown in FIG. 1). In another embodiment, more than one aperture can be employed, for example of differing diameters in order to de-convolve information about a location to be measured.

In this embodiment, measurement data associated with a probe beam is used to provide feedback information to guide a patient aligning to the optical system 100, though the feedback information can alternatively be used by another operator of the optical measurement apparatus, for example a clinician.

Consequently, a processing resource, for example a microprocessor 122 is coupled to the detector 112, an output device 124, for example an audible output module or a display device, being coupled to the processor 122. If required, a controller module or an interface module can be disposed between the processor 122 and the output device 124, though the interface module and/or the controller module can be integrally provided with the output device 124 or any other suitable functional entity of the optical measurement apparatus. The processor 122 is also coupled to a storage device 126, for example a non-volatile memory device, such as an Electrically Erasable Programmable Read Only Memory (EE-PROM).

In operation, the optical measurement apparatus is employed to make measurements in accordance with UK patent publication no. GB-B-2 407 378 or GB-A-2 409 033. However, operation of the apparatus is modified at the signal processing level. In this respect, a collimated probe beam 116 is emitted by the source 102 and directed to the scanning lens 106, where the collimated probe beam 116 is focused to a location to be measured 114.

The focussed probe beam 118 is reflected at the location to be measured 114, the reflected focussed probe beam 120 being incident upon the scanning lens 106 resulting in a collimated reflected beam 117. The collimated reflected beam 117 then passes through the beamsplitter 104 before being focussed upon the detector 112 by the focussing lens 108, the aperture 110 being confocal with the location to be measured 114 and thereby spatially limiting the region from which light is received.

As a result of incidence of the focussed reflected beam on the detector 112, the detector 112 generates an electrical output signal in response to the excitation of the detector 112 by the focussed reflected beam.

It should be appreciated that depending upon a degree of alignment of the location to be measured 114 with an optical receiving axis 115 of the optical system 114, the reflected collimated probe beam 117 will either be on-axis if the location to be measured 114 is aligned, or off-axis by varying amounts depending upon the degree of alignment (or misalignment) of the location to be measured 114 with the optical axis 115.

Figure 2:
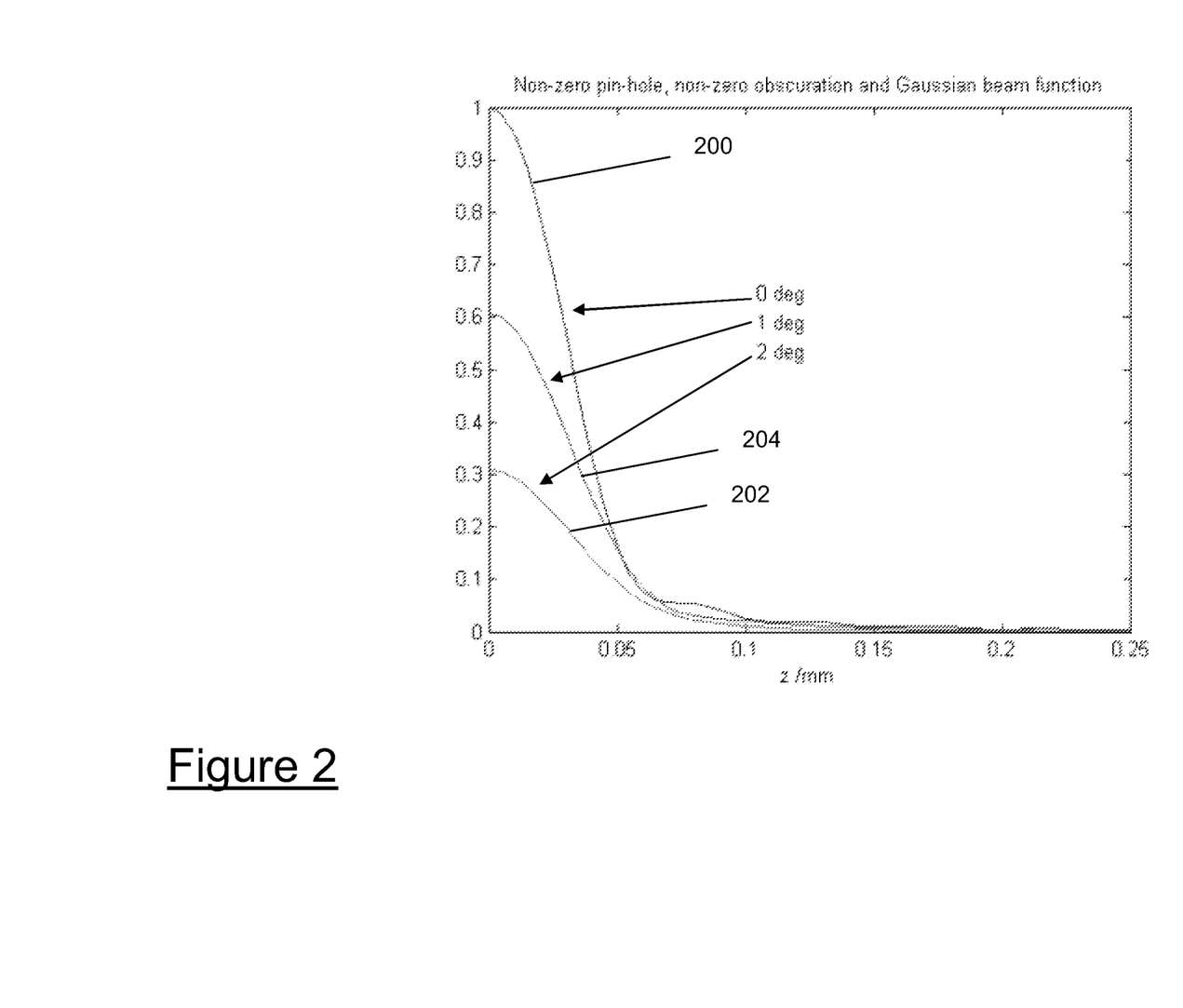
FIG. 2 is a calculated plot of a section of an expected output signal generated by a detector of FIG. 1.

Consequently, referring to FIG. 2, the electrical output signal will vary depending upon the degree of alignment of the location to be measured 114 with the optical axis 115. In this respect, a part of the output signal constitutes a response associated with the location to be measured 114 and generated in response to the focussed reflected probe beam being incident upon the detector 112. The response has a signal profile having certain characteristics that vary with the degree of alignment of the location to be measured 114 with the optical axis 115. Where the output signal is generated by the detector 112 as a result of multiple reflections incident upon the detector 112, the output signal is a varying signal that can be time-varying, varying as a function of distance or related to any other characteristic.

An assessment of one or more of the characteristics provides an indication of the degree of alignment. The assessment can be qualitative and/or quantitative, in this example by measurement of one or more parameters corresponding to a characteristic to be assessed, for example peak luminous intensity of the profile, tail luminous intensity of the profile, peak width of the profile, tail width of the profile, number of peaks in the trace, peak shape, peak location, inter-peak distance of the trace. The assessment can be performed in relation to a single or to consecutive traces so that both instantaneous and time based, integral or differential, measurements are possible. For the avoidance of doubt, a portion of a profile that constitutes a tail of the profile can be defined in a number of ways for assessment purposes. For example, the tail can be a lowest decile of a curve between predefined upper and lower limits, or a lowermost percentile between the limits. A starting point of the tail can be a point where a predetermined gradient is achieved, for example −1.

Additionally, or alternatively, the assessment can be based upon one or more differential, integral or other suitable mathematical functions applied to the above parameters, or integrals of a peak or a tail of a profile. In operation, the processor 122 makes a measurement in respect of the output signal and analyses the measurement to determine a quality factor in connection with the measurement made.

In a calibration mode, the optical measurement apparatus is initially calibrated, one or more measurements in respect of one or more locations to be measured being made when the one or more locations to be measured are known to be aligned with the optical axis 115. In this respect, profiles for one or more on-axis, i.e. substantially optimum, measurements are obtained for reference purposes, for example an on-axis profile 200. One or more characteristics of the profiles obtained are measured during calibration and stored in the storage device 126 accessible by the processor 122 for subsequent comparison purposes. Additionally or alternatively, parts of the profiles and/or characteristic data relating to the profiles or parts thereof can be stored in the storage device 126 as reference profile data and/or reference characteristic data for subsequent comparison purposes. If desired, the on-axis profile 200 can be modelled as opposed to employing empirical data. The model can take account of a number of system parameters, for example: beam size, beam intensity, beam profile, characteristics of one or more lenses, such as lens shape and/or angle of incidence of light being measured.

In a measurement mode (FIG. 3), after calibration, the location to be measured 114 is offered to the optical system 100, for example an eye having a surface 114 to be measured. Of course, a surface of the eye is only an example of the many items that can be measured. In this respect, a location in or on any suitable item under test, for example a physiological body-part can be measured using the optical system 100. The optical measurement apparatus is then used to make a measurement (Step 300) of the location to be measured 114. The output signal generated by the detector 112 is then measured and analysed (Step 302) by the processor 122 and one or more of the above-mentioned characteristic parameters are measured, for example, peak luminous intensity and/or a Q-factor of a first profile 202 constituting the output signal. These measured characteristic parameters are then compared (Step 304) with the corresponding pre-stored characteristic parameters and used to generate (Step 306) feedback information indicative of the closeness of match between the measured and stored qualitative characteristic parameters. If desired, one or more error values can be calculated as a result of the comparison and the feedback information generated by way of a function having the one or more error values as input values.

Figure 3:
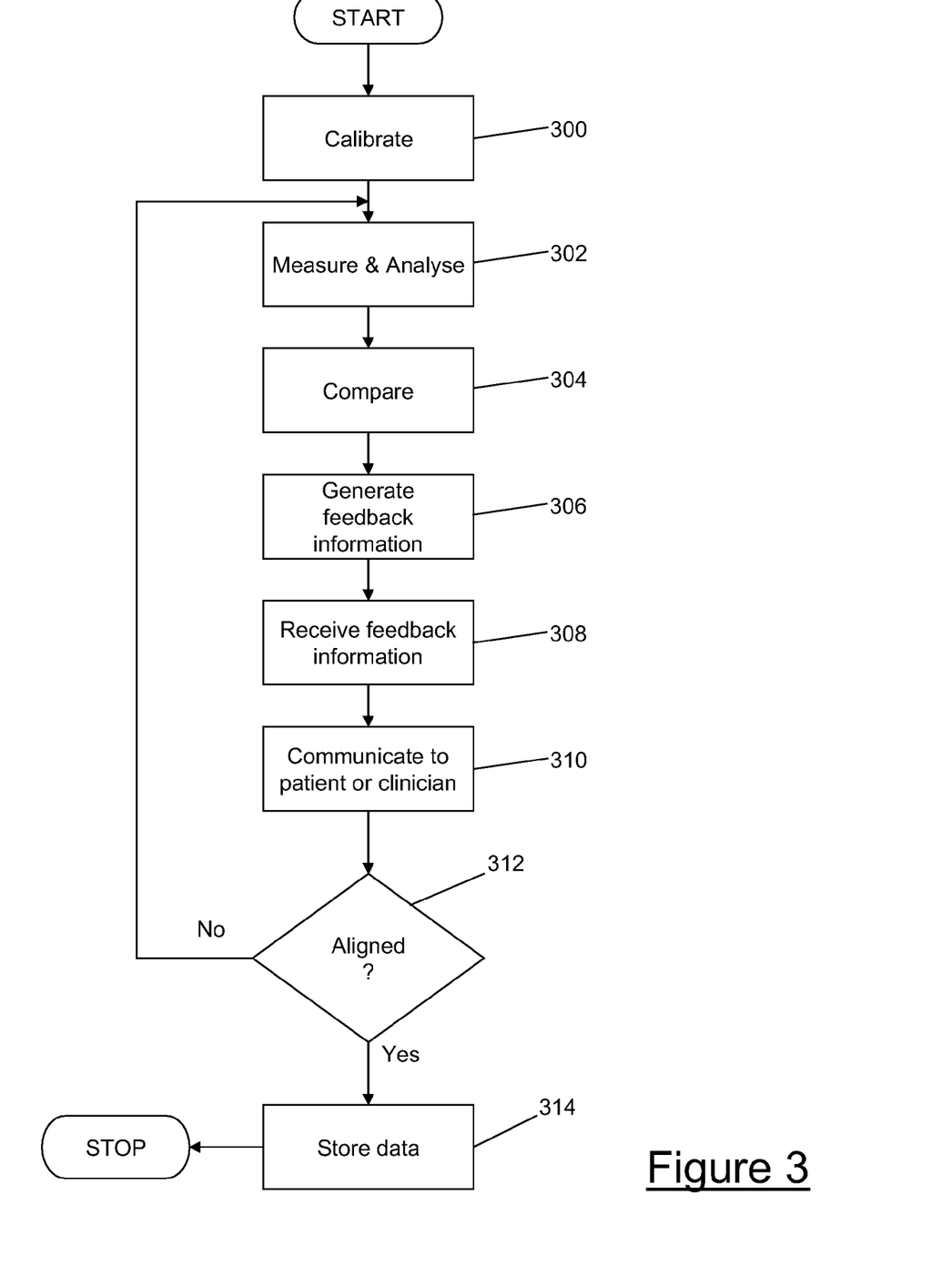
FIG. 3 is a flow diagram of an alignment method using the apparatus of FIG. 1.

The output device 124 then receives (Step 308) the feedback information and communicates the feedback information to the patient or the clinician as, for example, an audible feedback signal, visual feedback, such as a graphical presentation (assuming, in this example, the output device 124 is a display device interfaced with the optical system 100).

From this first iteration, the processor 122 determines (Step 312) that alignment of the location to be measured 114 with the optical axis 115 is poor due to the relatively low peak luminous intensity of the first profile 202 and so the degree of alignment is communicated to the patient and the patient knows to try to move, in this example, the eye to try to better align the location to be measured 114. The above measurement and comparison steps (Steps 302 to 312) are therefore repeated until adequate alignment is achieved. Consequently, a second profile 204 is now obtained in this example as a result of a second measurement made by the optical measurement apparatus. From this second iteration, the measured characteristics of the second profile 204 are sufficiently good to permit sufficiently accurate post-processing results to be achieved using the output signal corresponding to the second profile 204 and so alignment is deemed (Step 312) to be successful and positive feedback is accordingly provided. The measurement data obtained in respect of the second profile 204 is then stored (Step 314) in the storage device 126.

In another embodiment, the feedback information can also be used to weight measurement data obtained from the output signal. Also or alternatively, the feedback information can be used to look-up pre-stored correction factors to be applied to the measured profile 204.

In a further embodiment, the above technique can be modified to be a multiple stage alignment technique where a first characteristic is used to provide feedback information in order to achieve a coarse degree of alignment. Once the coarse alignment is achieved, a second characteristic is used to provide feedback information in order to achieve a finer degree of alignment.

In another embodiment, the output signal is a trace comprising more than one profile. Further, the trace comprises a summation of light returning from both corneal surfaces and the ocular lens surfaces of the eye is used to measure alignment of the eye with the optical axis 115 of the optical system 100. In this respect, the corneal surfaces and the ocular lens surfaces are naturally misaligned in both rotation and lateral location with respect to each other, the corneal and ocular surfaces having respective first and second axes. Consequently, the processor 122 can use this information to calculate the position and orientation of the eye as a whole or specifically the cornea or ocular lens with respect to the optical system 100 using measurements made in respect of different locations to be measured. Furthermore, the processor 122 can operate to achieve misalignment between the optical axis 115 and one of the first and second axes in order to obtain alignment of the optical axis 115 with the other of the first and second axes.

Figure 4:
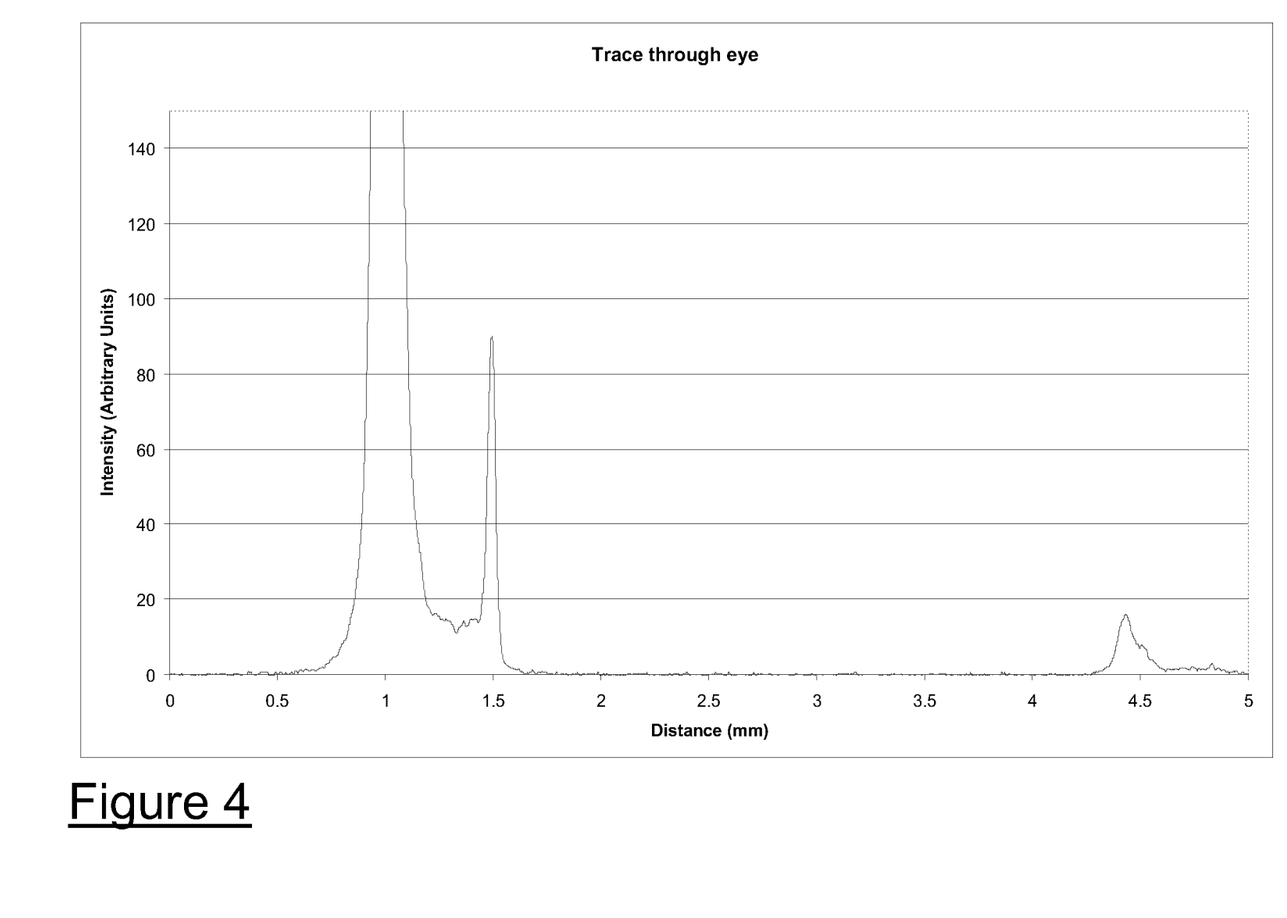
FIG. 4 is a plot of a trace generated by the detector of FIG. 1.

The measured trace comprises, in this example, a number of peaks relating to reflections at corneal and ocular lens surfaces (FIG. 4). Applying the calibration stage mentioned above to traces, an on-axis trace is recorded in the data store 126 corresponding to alignment of various locations in the eye with the optical axis 115 of the optical system 100. Once ideal traces are recorded, they can be compared (Step 304) with a measured trace in an analogous way to that described above. The feedback information is again an indication of closeness of fit between the measured and stored traces. It should be appreciated that the actual stored trace retrieved from the storage device 126 depends upon the specific location to be measured 114, for example a corneal surface.

Additionally or alternatively, the processor 122 can analyse a number of measurements made in order to detect motion of a patient, or more specifically, movement of the location to be measured 114 of the patient. The detected motion can be monitored to provide feedback in time to the patient as to alignment of the location to be measured 114 with the optical axis 115 and the future location of the location to be measured predicted. Beneficially, the patient can thus be informed not only that one or more measurements made are of a sufficiently good quality or of a bad quality, but also whether or not the quality of the measurements are improving as a result of the re-alignment being performed.

Instead of providing feedback, the above technique can be used simply to allow the patient to offer the eye comprising the location to be measured 114 to the optical system 100 of the optical measurement apparatus, the optical measurement apparatus making a number of measurements when alignment is both good and poor and simply rejecting one or more profiles obtained, or when measuring in relation to traces, one or more traces obtained and associated with misalignment of the optical system 100 with the eye. In this respect, a rejection threshold can be employed, the rejection threshold can, if desired, be based upon the qualitative or quantitative characteristic parameters mentioned above.

A benefit of this technique is that only good data is accepted and data that does not attain a desired quality is rejected, for example by thresholding, and does not undergo further time consuming analysis.

Figure 5:
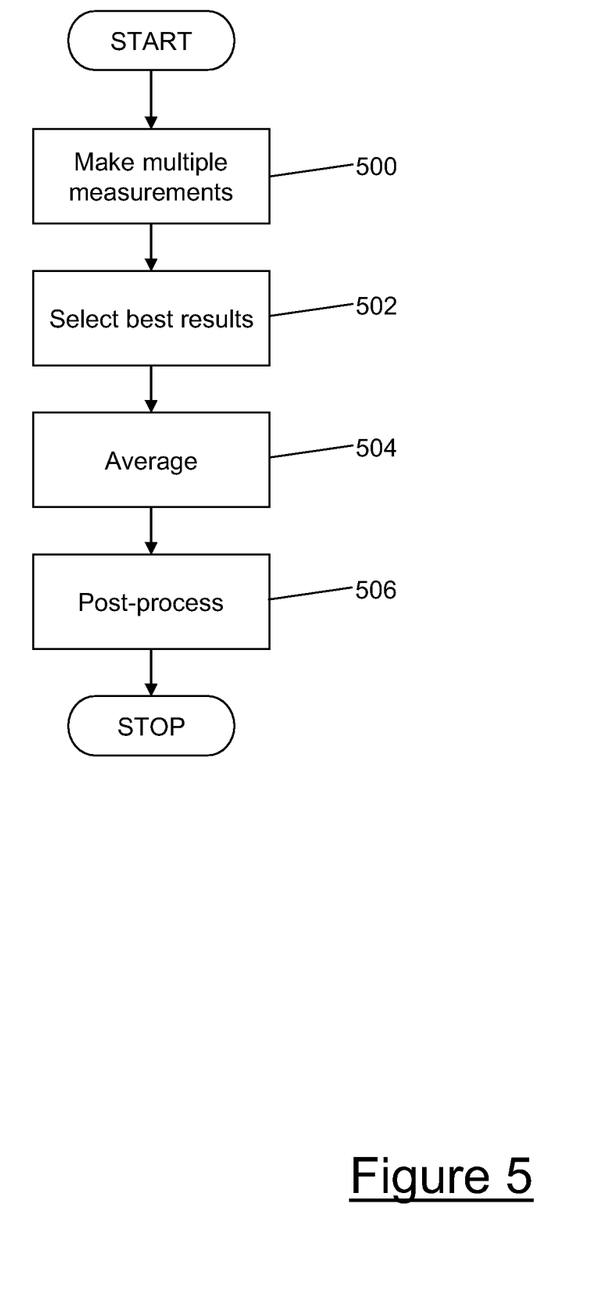
FIG. 5 is a flow diagram of a measurement technique using the apparatus of FIG. 1.

In yet another embodiment (FIG. 5), the optical system 100 is also arranged to make a number of sequential scans (Step 500). However, the processor 122 then filters the one or more profiles obtained, or when measuring in relation to traces, one or more traces obtained as a result of the multiple measurements using any of the techniques described above, for example using assessment of characteristic parameters and/or closeness of fit of profiles/traces with pre-stored data. The processor 122 then averages (Step 504) the remaining selected measurements before subjecting the average profile to post-processing (Step 506) where one or more aspects of the average trace is analysed to determine one or more physiological quantities associated with one or more locations to be measured, for example as described in UK patent publication no. GB-B-2 407 378 or GB-A-2 409 033. Such a technique removes the variability of the movement of the eye and reduces the electronic, optoelectronic and/or optical noise.

In all of the above techniques, any suitable statistical analysis can be used to determine closeness of fit, for example standard deviation calculations, least square algorithms or variance calculations.

Although the above examples have predominantly been described in the context of the human eye, the skilled person will appreciate that the techniques described herein can be employed in relation to measurement of any reflecting surface, for example any part of a body, be it human or otherwise.

Likewise, measurement of physiological parameters can be made using the above techniques in relation to the body. One example of the physiological parameter is a blood-glucose concentration.

The optical measurement apparatus can be provided as a portable apparatus for personal or clinical use, for example a hand-held device, or table, desk or bench-top apparatus for a clinical environment where a clinician can be present.

In any of the above-described alignment techniques, the skilled person should appreciate that one eye can be used for alignment and another eye for measurement. Alternatively, both eyes can be used for alignment purposes, thereby improving comfort to the subject and hence reduce the motion in the eye.

It should be appreciated that references herein to "light", other that where expressly stated otherwise, are intended as references relating to the optical range of the electromagnetic spectrum, for example, between about 350 nm and about 2000 nm, such as between about 550 nm and about 1400 nm or between about 600 nm and about 1000 nm.

Alternative embodiments of the invention can be implemented as a computer program product for use with a computer system, the computer program product being, for example, a series of computer instructions stored on a tangible data recording medium, such as a diskette, CD-ROM, ROM, or fixed disk, or embodied in a computer data signal, the signal being transmitted over a tangible medium or a wireless medium, for example, microwave or infrared. The series of computer instructions can constitute all or part of the functionality described above, and can also be stored in any memory device, volatile or non-volatile, such as semiconductor, magnetic, optical or other memory device.

What is claimed is:

1. An optical measurement apparatus comprising:
   an optical system comprising:
   a source arranged to generate, when in use, a probe beam, the optical system being arranged to direct, when in use, the probe beam to a location to be measured;
   a detector arranged to receive, when in use, a reflected beam from the location to be measured; and
   a receiving axis;
   wherein the apparatus further comprises:
   a processing resource operably coupled to the detector and capable of assessing when in use, a characteristic of an output generated by the detector, assessment of the characteristic of the output corresponding to an assessment of degree of alignment of the location to be measured with the receiving axis of the optical system; and
   a store for storing reference profile data corresponding to at least part of a profile and/or reference characteristic data relating thereto, the reference profile data and/or the reference characteristic data corresponding to a state of alignment with the optical system;
   wherein the processing resource is arranged to make the assessment of the degree of alignment based upon comparison of at least part of the signal profile and/or characteristic data relating thereto in respect of the output measured and the stored reference profile data and/or the stored reference characteristic data.

2. An apparatus as claimed in claim 1, wherein the assessment of the characteristic of the output is assessment of a parameter measured and corresponding to the characteristic of the output.

3. An apparatus as claimed in claim 1, wherein:
   the processing resource is arranged to provide feedback information indicative of the degree of alignment of the location to be measured with the receiving axis, the feedback information being based upon the assessment of the characteristic of the output.

4. An apparatus as claimed in claim 3, wherein the location to be measured is a location of a feature of an eye having a first axis and a second axis, the processing resource being arranged to provide feedback to obtain a misalignment of the first axis with the receiving axis in order to achieve alignment of the second axis with the receiving axis.

5. An apparatus as claimed in claim 3, wherein the feedback information is an audible or visual indication of alignment.

6. An apparatus as claimed in claim 1, wherein the location to be measured is a location of a feature of an eye and the probe beam is invisible to the eye.

7. An apparatus as claimed in claim 1, wherein the processing resource is arranged to perform a measurement in respect of the reflected beam and generate a first measure of the characteristic of the output.

8. An apparatus as claimed in claim 7, wherein the processing resource is arranged to generate a second measure of another characteristic of the output.

9. An apparatus as claimed in claim 7, wherein the first measure is used to provide a coarse indication of the degree of alignment of the location to be measured with the optical system.

10. An apparatus as claimed in claim 8, wherein the second measure is used to provide a fine indication of the degree of alignment of the location to be measured with the optical system.

11. An apparatus as claimed in claim 1, further comprising a store for storing data corresponding to a state of substantially optimum alignment with the optical system.

12. An apparatus as claimed in claim 1, wherein the output of the detector has a signal profile corresponding to a reflection of the probe beam in respect of the location to be measured.

13. An apparatus as claimed in claim 12, wherein the output of the detector is a trace comprising a number of profiles and/or characteristics respectively corresponding to a number of reflections of the probe beam.

14. An apparatus as claimed in claim 13, wherein the number of reflections comprises a first reflection from the location to be measured and another location to be measured, the locations to be measured being misaligned with respect to each other.

15. A method of optical measurement, comprising:
   generating a probe beam;
   directing the probe beam to a location to be measured;
   receiving via an optical system having a receiving axis a reflected beam from the location to be measured;
   assessing with a processing resource a characteristic of an output signal corresponding to the reflected beam in order to determine the degree of alignment of the location to be measured with the receiving axis of the optical system;
   storing reference profile data corresponding to at least part of a profile and/or reference characteristic data relating thereto, the reference profile data and/or the reference characteristic data corresponding to a state of alignment with the optical system; and
   the processing resource making the assessment of the degree of alignment based upon comparison of at least part of the signal profile and/or characteristic data relating thereto in respect of the output measured and the stored reference profile data and/or the stored reference characteristic data.

16. An optical measurement apparatus comprising:
an optical system comprising:
- a source arranged to generate, when in use, a probe beam, the optical system being arranged to direct, when in use, the probe beam to a location to be measured;
- a detector arranged to receive, when in use, a reflected beam from the location to be measured; and
- a receiving axis;

wherein the apparatus further comprises:
- a processing resource operably coupled to the detector and capable of assessing when in use, a characteristic of an output generated by the detector, the output of the detector having a signal profile corresponding to a reflection of the probe beam in respect of the location to be measured; wherein
- the signal profile is generated by acquiring a number of sequential profiles over a period of time using the probe beam and processing a number of output signals corresponding to the sequential profiles; and
- assessment of the characteristic of the output corresponds to an assessment of degree of alignment of the location to be measured with the receiving axis of the optical system.

17. An apparatus as claimed in claim 16, wherein the processing of the number of output signals comprises filtering the number of output signals so as to discard any output signals having respective degrees of alignment that do not conform to a predetermined alignment degree threshold.

18. An apparatus as claimed in claim 16, wherein the processing of the number of output signals comprises averaging undiscarded output signals from the number of output signals.

* * * * *